US009855076B2

(12) United States Patent
Nichols et al.

(10) Patent No.: US 9,855,076 B2
(45) Date of Patent: *Jan. 2, 2018

(54) ROD COUPLING SYSTEMS AND DEVICES AND METHODS OF MAKING AND USING THE SAME

(71) Applicant: GLOBUS MEDICAL, INC., Audubon, PA (US)

(72) Inventors: Jeff Nichols, Philadelphia, PA (US); Fred Harderbrook, Sicklerville, NJ (US); Aditya Ingalhalikar, Bryn Mawr, PA (US); Mark Fromhold, Ardmore, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/148,333

(22) Filed: May 6, 2016

(65) Prior Publication Data

US 2016/0317189 A1 Nov. 3, 2016

Related U.S. Application Data

(63) Continuation of application No. 13/731,252, filed on Dec. 31, 2012, now Pat. No. 9,358,046.

(51) Int. Cl.
*A61B 17/70* (2006.01)

(52) U.S. Cl.
CPC ...... *A61B 17/7032* (2013.01); *A61B 17/7002* (2013.01); *A61B 17/7004* (2013.01); *A61B 17/7037* (2013.01)

(58) Field of Classification Search
CPC ............ A61B 17/7032; A61B 17/7002; A61B 17/7004; A61B 17/7037
USPC .................. 606/246, 264–272, 278, 279, 328
See application file for complete search history.

(56) References Cited

U.S. PATENT DOCUMENTS

| 8,236,035 | B1 | 8/2012 | Bedor |
| 9,358,046 | B2 * | 6/2016 | Nichols ............. A61B 17/7004 |
| 2005/0131410 | A1 | 6/2005 | Lin |
| 2010/0100136 | A1 | 4/2010 | Won et al. |
| 2010/0114170 | A1 | 5/2010 | Barrus et al. |
| 2010/0234891 | A1 | 9/2010 | Freeman et al. |

(Continued)

FOREIGN PATENT DOCUMENTS

EP          1795134 B1     8/2008

*Primary Examiner* — Pedro Philogene
*Assistant Examiner* — David C Comstock

(57) ABSTRACT

Provided are rod coupler devices, systems, kits and methods, which include at least one saddle having a concave configuration that either abuts a bone fastener and/or a locking cap and is shaped so as to contact the rod in two or more lines of contact, which reduces pressure on the rod, and therefore permits use of a rod having various materials, such as PEEK, without significant deformation of the rod. Also provided is the saddle itself and integrated locking caps that include a saddle, the locking cap and a set screw. Also provided are elongate rods having advantageous shapes, configurations, and/or compositions for rod coupler devices, systems and methods. Further provided are screw and cap devices and systems that themselves include a concave configuration so as to contact a rod in two or more lines of contact, which reduces pressure on the rod.

20 Claims, 12 Drawing Sheets

(56) References Cited

U.S. PATENT DOCUMENTS

2012/0041490 A1 2/2012 Jacob et al.
2012/0253409 A1 10/2012 Peterson et al.

* cited by examiner

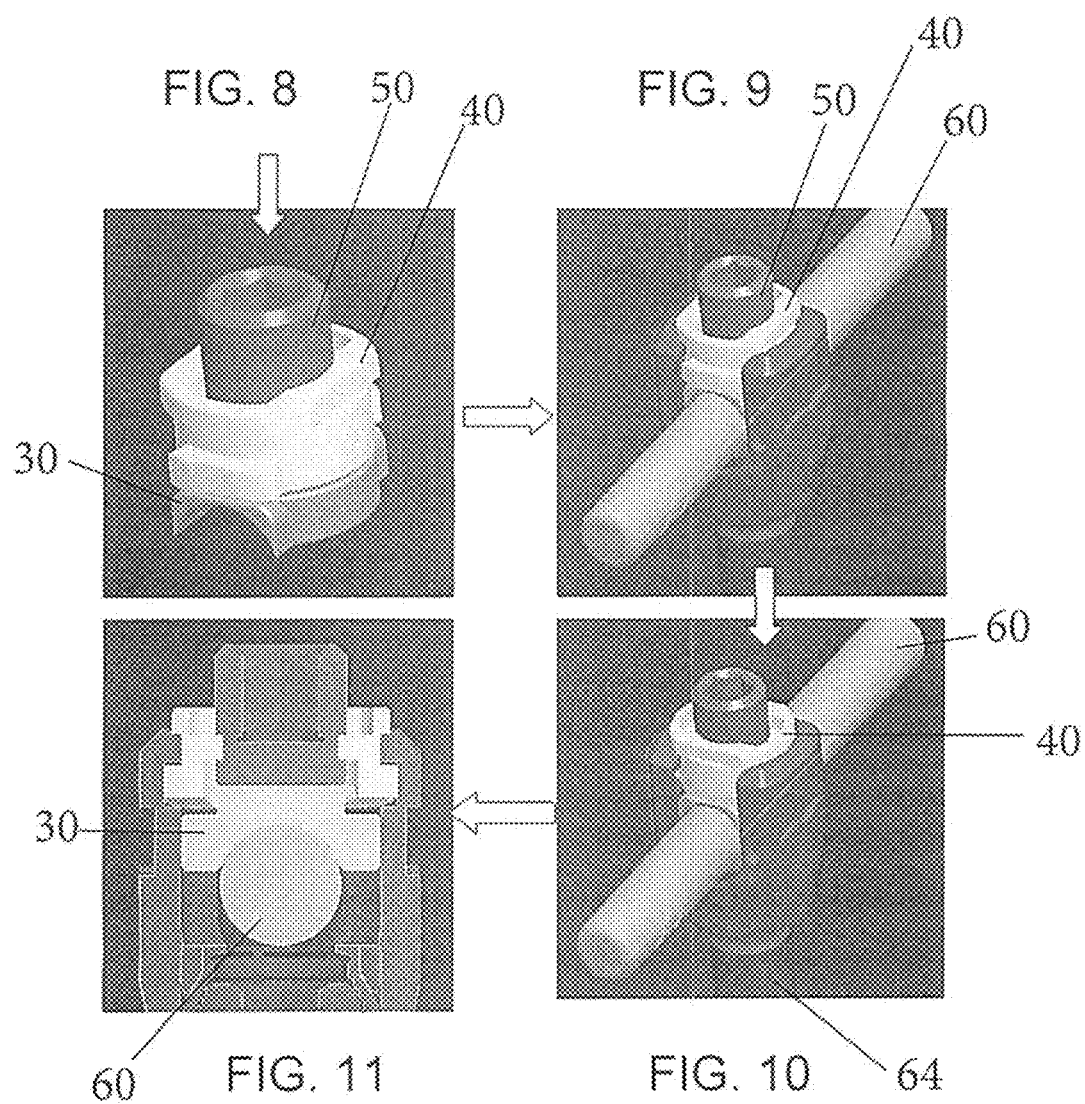

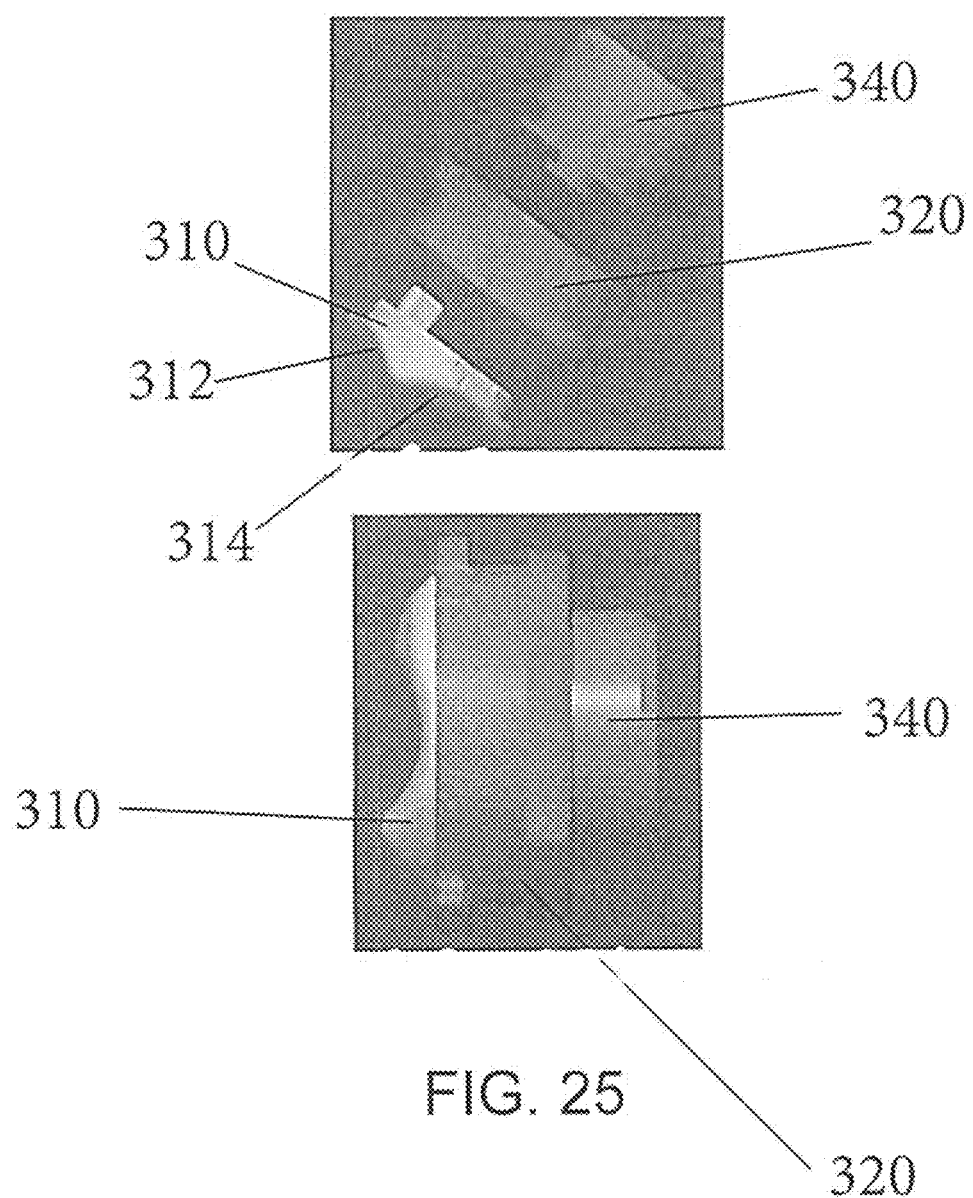

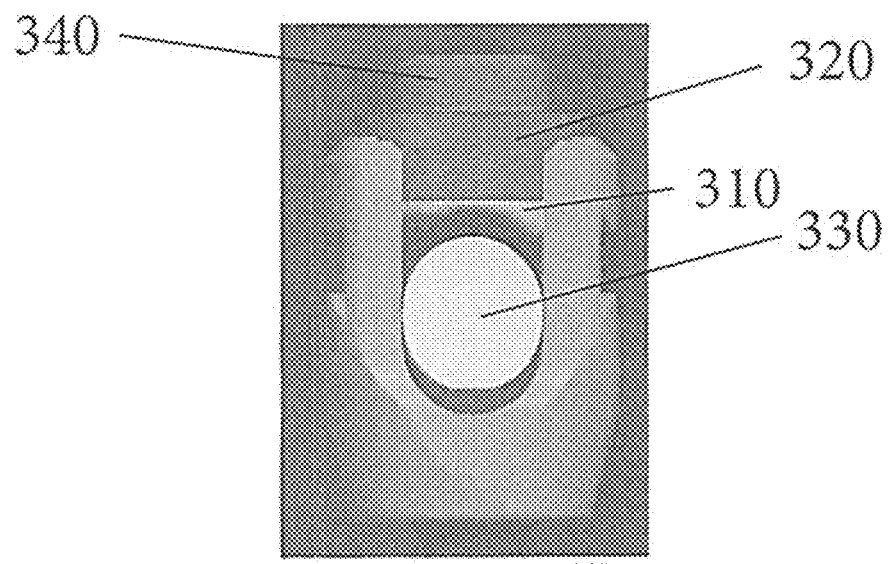
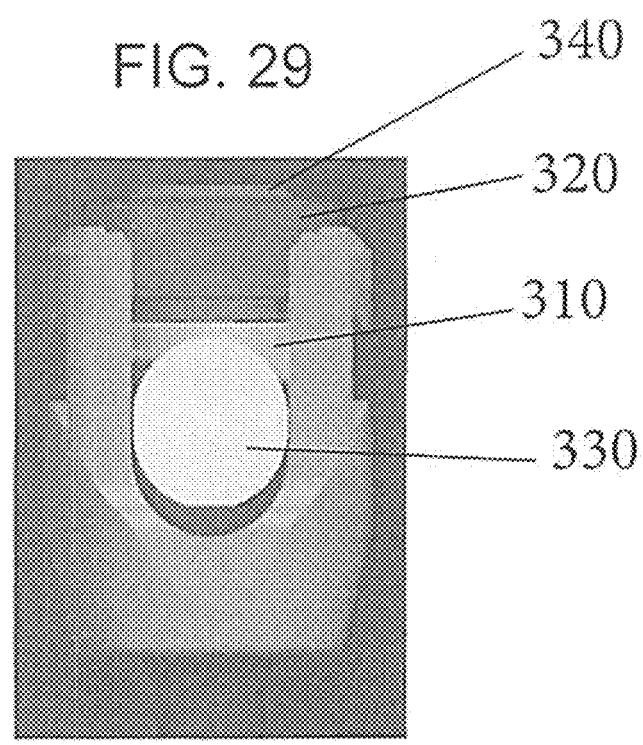

ROD COUPLING SYSTEMS AND DEVICES AND METHODS OF MAKING AND USING THE SAME

CROSS-REFERENCE TO RELATED APPLICATION

This application is a continuation of U.S. application Ser. No. 13/731,252 filed Dec. 31, 2012, which is incorporated by reference herein in its entirety for all purposes.

TECHNICAL FIELD

The present invention relates to orthopedic rod coupler systems, devices, kits, and methods. Examples include a saddle configured to attach to either a bone fastener or a locking cap of the rod coupler system and having a concave portion configured to increase surface area of contact with a rod so as to reduce pressure on the rod, particularly when the rod is tightened within the rod coupler system. Other examples include bone fasteners or caps that themselves are configured to have a concave portion, which increases surface area of contact with a rod. The reduced pressure on the rod enables use of rods of various compositions, including Polyether ether ketone ("PEEK"), without deformation of the rod. The invention also relates to elongate rods having advantageous shapes, configurations, and/or compositions for rod coupler devices, systems and methods.

BACKGROUND

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of bone fasteners such as screws and/or hooks to one or more vertebrae and connecting the screws or hooks to an elongate rod that generally extends in the direction of the axis of the spine.

Treatment for these spinal irregularities often involves using a system of pedicle screws and rods to attain stability between spinal segments. Such systems may provide support or stability to the spinal bone structure, which may promote healing of the bone structures and/or otherwise maintain alignment and spacing of the spinal bone structures. Instability in the spine can create stress and strain on neurological elements, such as the spinal cord and nerve roots. In order to correct this, implants of certain stiffness can be implanted to restore the correct alignment and portion of the vertebral bodies. In many cases, an anchoring member such as a pedicle screw along with a vertical solid member can help restore spinal elements to a pain free situation, or at least may help reduce pain or prevent further injury to the spine.

The screw systems can include coupling members that attach pedicle screws to rods. There is a need for improved coupling members to accommodate different types of rods.

SUMMARY

Existing bone screws systems may be used to secure a rod between two surfaces. For example, systems can include a coupling member that receives a locking cap, whereby a rod is secured between a flat surface of the coupling member and a flat surface of the locking cap. This creates a small area of contact along the line of tangency on both sides of the rod, and thus puts a large amount of pressure on the rod. When used with a non-titanium rod, such as a PEEK rod, this configuration plastically deforms the rod. PEEK is a very notch sensitive material, and this deformation greatly reduces the mechanical strength of the rod.

The present inventions generally solve the problem of being able to use PEEK rods with pedicle screws and rod coupler systems (including existing pedicle screws and rod coupler systems). Examples of the current devices, systems and methods involve a specially designed saddle insert, locking cap, and/or unique rod shapes, which increase the surface area contact with rods, such as rods including PEEK, to reduce notching of the rod. The present inventions may also include a new bone fastener, such as a screw, with the specialized geometry of the insert, e.g., a concave portion incorporated into the screw itself. The bone fastener can optionally be used e.g., in conjunction with the specialized locking cap to increase surface area contact on multiple sides of the rod.

In non-limiting example embodiments, rod coupler systems may include a coupling body having a bone fastener disposed therethrough, and a saddle having a first side of the saddle abutting the bone fastener within the coupling body, and a second side of the saddle opposite the first side, having a concave portion configured to abut an elongate rod along at least two lines of contact between the saddle and the rod.

According to other example embodiments, a rod coupler system is provided which includes a coupling body having a bone fastener disposed therethrough, a locking cap adapted for attachment to the coupling body, and a saddle having a first side of the saddle abutting the locking cap, and a second side of the saddle opposite the first side, the second side having a concave portion configured to abut an elongate rod along at least two lines of contact between the saddle and the elongate rod.

Also provided are saddles that include a first side configured to be attached to a bone fastener or to a locking cap for a coupling body; and a second side opposite the first side of the saddle, the second side having a concave portion configured to abut an elongate rod along at least two lines of contact between the saddle and the elongate rod.

Also provided are integrated locking caps that include a locking cap adapted for attachment to a coupling body, and a saddle having a first side of said saddle removably attached to the locking cap, a second side of the saddle opposite the first side, the second side having a concave portion configured to receive and abut an elongate rod along at least two lines of contact between the saddle and the elongate rod, and a set screw disposed through the locking cap.

Further example embodiments include polyaxial screws and locking caps having a concave portion configured to abut an elongate rod along at least two lines of contact between the polyaxial screw and/or the locking cap and the rod.

Other example embodiments include kits that include one or more components of the present devices and systems. For example, kits may include a coupling body and a saddle, or they may include a locking cap and a saddle. Kits may include many other possible components as well. At least two components may be preassembled together within the kit.

The foregoing has outlined rather broadly the features and technical advantages of the present invention in order that the detailed description of the invention that follows may be better understood. Additional features and advantages, which form the subject of the claims of the invention, will be described herein. It should be appreciated by those skilled in the art that any specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF THE DRAWINGS

Non-limiting example embodiments described herein, with reference to the following accompanying Figures.

FIG. 8 depicts a perspective view of the integrated locking cap assembly of FIG. 7, in which the saddle is engaged with the locking cap.

FIG. 9 depicts a perspective view of a pedicle screw assembly having a rod inserted therein and the integrated locking cap assembly of FIG. 8 inserted over the rod.

FIG. 10 depicts a perspective view of the pedicle screw assembly having a rod inserted therein and the integrated locking cap assembly of FIG. 8 inserted over the rod, in which the cap is rotated to lock the cap onto the screw head.

FIG. 11 depicts a cross sectional front view of the assembly of FIG. 10 in which the integrated locking cap depicted e.g., in FIG. 8 is configured in a pedicle screw assembly over an elongate rod.

FIG. 24 depicts a perspective exploded view of an integrated saddle-locking cap in accordance with non-limiting example embodiments.

FIG. 25 depicts a side view of the integrated saddle-locking cap of FIG. 24, fully assembled.

FIG. 28 depicts a front view of a saddle-locking cap design inserted into a standard screw head, which has been rotated 90 degrees and locked into place.

FIG. 29 depicts a front view of a saddle-locking cap design, in which a set screw has been tightened and the saddle abuts the rod, locking the rod.

DETAILED DESCRIPTION

Figure 1:
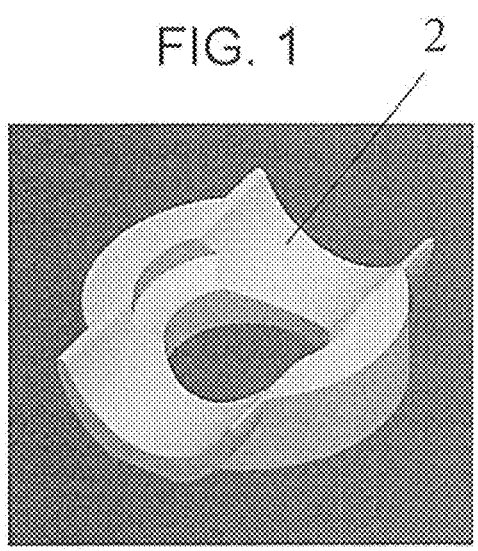
FIG. 1 depicts a perspective view of a saddle that may be used in example embodiments of the present devices and systems.

The aspects, advantages and/or other features of example embodiments of the invention will become apparent in view of the following detailed description, taken in conjunction with the accompanying drawings. In describing example embodiments, specific terminology is employed for the sake of clarity. However, the embodiments are not intended to be limited to this specific terminology. It should be apparent to those skilled in the art that the described embodiments of the present invention are merely exemplary and illustrative and not limiting. Numerous embodiments of modifications thereof are contemplated as falling within the scope of the present invention and equivalents thereto. It is to be understood that each specific element includes all technical equivalents that operate in a similar manner to accomplish a similar purpose.

Unless otherwise noted, technical terms are used according to conventional usage.

As used herein, "a" or "an" may mean one or more. As used herein, "another" may mean at least a second or more. Furthermore, unless otherwise required by context, singular terms include pluralities and plural terms include the singular.

As indicated above, the present inventions generally solve the problem of being able to use PEEK rods, or rods of other materials, with pedicle screws and rod coupler systems by increasing contact area with the rods and thereby reducing pressure on the rods. In some embodiments, a polyaxial pedicle screw made of titanium is provided as part of the coupling system, which is highly resistant to corrosion and fatigue, and is MM compatible. The screw is threaded and the head is mobile—it swivels helping to defray vertebral stress. Like other screws, polyaxial screws come in many sizes. In some embodiments, a polyaxial pedicle screw length ranges from 30 mm to 60 mm (up to 2½ inches). In some embodiments, the diameter ranges from 5.0 mm to 8.5 mm (up to ¼ inch). Polyaxial pedicle screws are used to correct deformity, and/or treat trauma. Similar to other bone screws, pedicle screws may be used in instrumentation procedures to affix rods and plates to the spine. The screws may also be used to immobilize part of the spine to assist fusion by holding bony structures together. However, when such screws are used on rod coupling systems, the rod needs to be equally strong, so that plastic deformation of the rod does not occur upon tightening of the rod to the system.

FIGS. 1-13 depict non-limiting example embodiments of rod coupling devices, systems and methods configured to increase surface area between the locking cap or the screw head and the rod, and therefore decrease plastic deformation of the rod. Such devices and systems may include for example a saddle insert, an integrated locking cap, and/or a screw head having an incorporated saddle geometry.

The present embodiments allow pedicle screw systems to become compatible with the use of PEEK rods, increasing the versatility of the screw systems. The present embodiments are advantageous e.g., in that they accommodate the use of various instrumentation used by surgeons. In some embodiments, the PEEK rod constructs described herein can be revised to be formed at least in part by titanium as well as other biocompatible materials, such as stainless steel and alloys.

In example embodiments, rod coupler systems may include a coupling body having a bone fastener, such as a pedicle screw, disposed therethrough, and a saddle having a first side of the saddle abutting the bone fastener within the coupling body, and a second side of the saddle opposite the first side, having a concave portion configured to abut an elongate rod along at least two lines of contact between the saddle and the rod.

Figure 2:
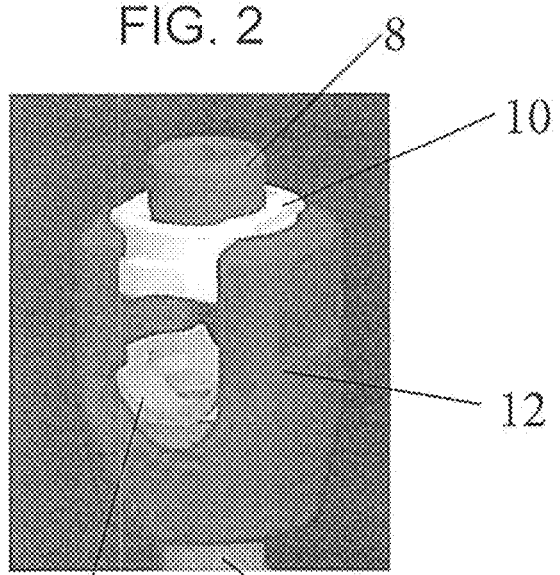
FIG. 2 depicts a perspective view of a pedicle screw having the saddle of FIG. 1 inserted therein in accordance with embodiments of the present devices and systems.
Figure 3:
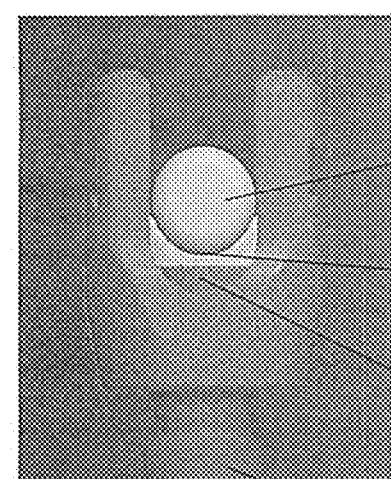
FIG. 3 depicts a front view of the pedicle screw of FIG. 2, having a rod inserted therein.

FIGS. 1-3 depict non-limiting example embodiments of saddle insert rod coupler systems in accordance with non-limiting example embodiments of the present invention. In particular, these embodiments depict a saddle 2 having a concave surface that essentially corresponds to the diameter of an elongate rod 4, such as a PEEK rod, to be used. The saddle 2 can be inserted e.g., into the bottom of a pedicle screw assembly. The saddle's shape 2 serves to increase the surface area contact between the top of the saddle 2 (and therefore between the top of the screw head 6A of a pedicle screw 6) and the bottom of the rod 4A. This increased surface area decreases the pressure on the rod when a set screw 8 (such as a hexagonal set screw) is finally tightened, eliminating significant plastic deformation of the rod. The saddle insert 2 may be inserted into the screw head with a slight press fit to maintain its positioning, and features into the rod slot in the screw head to prevent axial rotation. According to example methods, the insert saddle 2 may be placed in the assembly before screw insertion into the pedicles of a patient.

FIG. 1 depicts a perspective view of the saddle 2 before insertion into a pedicle screw assembly or system. As shown in FIG. 2, according to example embodiments, a set screw 8 disposed in a cap 10 of a coupling body 12, may be used to apply downward pressure on an elongate rod 4, disposed between the saddle 2 and the cap 10, to hold the rod 4 firmly in position. The placement of a rod in the saddle 2 is depicted in FIG. 3, (the end of the rod being depicted in this front view), prior to a locking cap and or set screw being placed thereover.

According to non-limiting example embodiments a coupling body may include an inner surface portion at a lower end of the coupling body. The inner surface portion may be configured for example to receive or engage the fastener. The coupling body may further have at least two sidewalls that define two upwardly extending arms that define two slots capable of receiving the elongate rod. The coupling body (e.g., element 12 in FIG. 2) may be e.g., of a tulip shape for example, and may include a first and second opening in the sidewalls that are configured to receive the elongate rod. As depicted for example in FIGS. 2 and 12. The saddle should be configured such that the concave portion aligns with the slit of the coupling body, thus allowing the rod to fit within the concave portion of the saddle while the saddle is within the coupling body.

According to non-limiting example embodiments, a cap may engage with an upper end of the coupling body and capture an elongate rod within a recess of an inner surface portion of the elongate body. The cap may be configured so as to be capable of applying a downward force upon the elongate rod.

According to example embodiments, the coupling body may include at least one groove disposed about an interior sidewall of the coupling body. The cap may include at least one tongue configured to ride within the groove of the coupling body. The cap may also include a lip that engages the upper end of the coupling body to align the tongue of the cap and the groove of the coupling body when the cap is inserted into the coupling body. According to alternative embodiments, the coupling body may include at least one tongue and the cap may include at least one groove, wherein the tongue of the coupling body rides within the groove of the cap. These and various other methods and configurations for engaging a cap with a coupling body may be within the skill of those in the art and all such embodiments are intended to be encompassed by the present embodiments.

With reference to the figures as non-limiting examples, a locking cap 10 may be provided that allows the user to easily insert the cap into the coupling body 12. For example, with reference to FIG. 2, a cap 10 is provided that may be placed within the coupling body 12. In these example embodiments, the cap 10 may generally match the shape of coupling body 12. The cap 10 is configured to fit substantially within the interior side walls of the coupling body 12. It should be understood that alternative designs and shapes may be used. A set screw 8 may be disposed in the locking cap.

According to non-limiting example embodiments, rotation of the cap to a second position relative to the coupling body presses an elongate rod against at least one saddle e.g., a saddle abutting said bone fastener and/or a saddle adjacent to or otherwise configured with said cap, so that the at least one saddle abuts said rod, and locks the coupling body and rod in position relative to one another and relative to the bone fastener.

The cap may include a locking element capable of securely holding the elongate rod in a fixed position relative to the coupling body. The cap may include a threaded opening and the locking element comprises a threaded set screw disposed within the threaded opening, wherein the set screw is capable of applying downward pressure on the elongate rod to lock the elongate rod in position.

According to example embodiments, the cap and coupling body may be configured with at least one detent and corresponding recess that contact each other when the cap is in the second position to resist inadvertent loosening of the cap from the coupling body. Rotation of the cap toward to the second position may cause the detent and corresponding recess to provide a tactile or audible signal to the physician, so a physician is aware that the two are essentially locked with respect to one another.

In some embodiments, the cap may include a sidewall having a first and second channel formed therein, wherein the first and second channels are wider than the diameter of the elongate rod. The first and second channels may be configured to permit the cap to rotate from e.g., 5-90 degrees or 20-40 degrees when in communication with the coupling body without being impeded by the elongate rod. According to example embodiments, the cap may be configured to provide a tactile or audible click when rotated to the second position.

Bone fasteners according to the present invention may include any bone fastener known to those skilled in the art. According to non-limiting example embodiments, the bone fastener may be a pedicle bone screw having a head. Non-limiting example screws may be made of any suitable material, including for example titanium. Example screws may also be of any size and/or configuration known to those skilled in the art. Additionally, example screws may have various diameters, such as substantially uniform diameters, or they may have two or more diameters or may be tapered.

Rod coupling systems provided herein may further include one or more of a locking cap, a set screw disposed in the locking cap, and an elongate rod.

Also provided are devices that include a bone fastener and a saddle attached thereto, in which the saddle has a first side that abuts the bone fastener and a second side opposite said first side, which second side has a concave portion that is configured to receive and support a rod along at least two lines of contact between said saddle and said rod.

According to non-limiting example embodiments, the concave portion of the saddle may be shaped so as to substantially correspond to a portion of surface area of the elongate rod. For example, as depicted in FIG. 3, according to non-limiting example embodiments, a surface portion of a bottom of the rod may substantially correspond to the curvature of the concave portion of the saddle, such that much of the corresponding surface portion of the rod is in contact with the saddle and pressure may be distributed over the areas in contact.

The saddle insert devices and systems increase contact through a step of placing the insert into the bottom of the screw head before it is inserted into the pedicle of a patient.

According to example embodiments, the saddle (e.g., either abutting the bone fastener or abutting or integrated with a locking cap), may have a smaller radius than the radius of an elongate rod to be inserted therein.

Rods according to the present invention may be any suitable size in length and/or diameter and may include for example a PEEK material, or a combination of PEEK and another ingredient. Non-limiting examples of rods that may be used in accordance with the present invention may include for example any rod configured for use with bone screws.

The rod may contain PEEK as a component thereof. According to non-limiting example embodiments, at least part of the rod is made of PEEK. Example rods may include for example titanium rods, rods that include PEEK on the outside of the rod, for example in the form of a tube, with titanium therein for example by a titanium rod of a desired size being inserted into the PEEK tube. Example rods may be of any suitable shape or design for use in conjunction with bone screws. The shape of example rods may be for example in a generally elongate shape. Further examples of rods that may be used in accordance with the inventions herein are provided herein below.

Further provided are methods that include inserting a saddle into a coupling body such that the saddle abuts a bone fastener in the coupling body on a first side of the saddle, and wherein the saddle has a second side opposite said first side, which second side has a concave portion that is configured to abut a rod along at least two lines of contact between the saddle and said rod. The present methods may further include inserting the bone fastener into a patient, adding an elongate rod to the bone fastener such that the elongate rod abuts the saddle and adding a cap over the rod. The methods may further include securing the cap and/or tightening the cap over the rod.

According to example embodiments of integrated locking caps, a rod coupler system is provided which includes a coupling body having a bone fastener disposed therethrough, a locking cap adapted for attachment to the coupling body, and a saddle having a first side of the saddle abutting the locking cap, and a second side of the saddle opposite the first side, the second side having a concave portion configured to abut an elongate rod along at least two lines of contact between the saddle and the elongate rod. Such example systems may further include a set screw.

FIGS. 4-11 depict non-limiting examples of integrated locking cap embodiments of the present invention. According to these example integrated locking cap embodiments, the saddle 30 may be built into or added to the cap 40 itself, prior to insertion into a patient, thus eliminating any potential extra steps in surgery.

According to non-limiting example embodiments, screw head design may allow for the surface area contact on both sides of the rod to be increased, thus reducing or eliminating plastic deformation.

Figure 4:
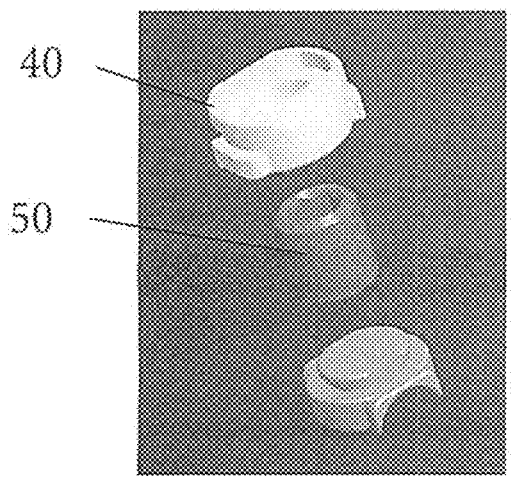
FIG. 4 depicts an exploded view of an integrated locking cap assembly according to example embodiments of the present devices and systems.
Figure 5:
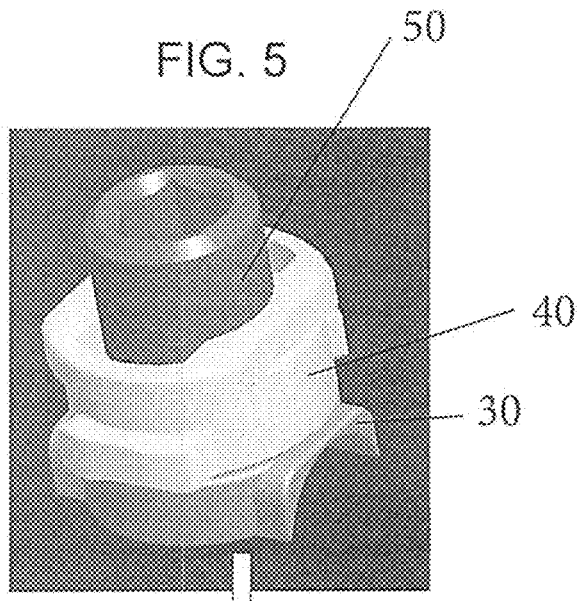
FIG. 5 depicts a perspective view of an assembled integrated locking cap assembly having the components depicted in FIG. 4.

According to the examples depicted in FIGS. 4-11, a saddle 30 essentially matching the diameter of a PEEK rod 60 to be used, is fixed (possibly temporarily or removably fixed) to a modified locking cap 40. FIG. 4 depicts an exploded view of an integrated locking cap assembly. In particular, FIG. 4 depicts a cap 40, which is configured to be attachable to a saddle 30, and may have a set screw 50 disposed through said cap. FIG. 5 depicts a perspective view of an assembled integrated locking cap assembly having the components depicted in FIG. 4.

Figure 7:
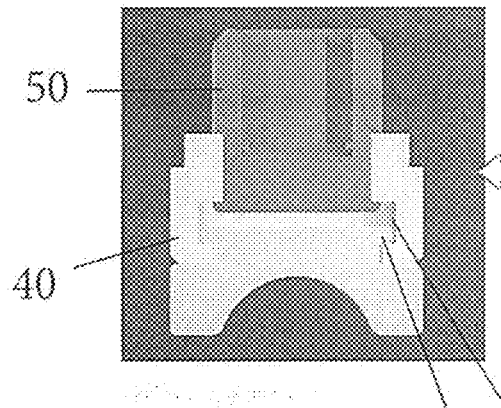
FIG. 7 depicts a cross sectional view of the integrated locking cap assembly of FIG. 6, in which the saddle is turned 90 degrees to engage the saddle with the locking cap.
Figure 6:
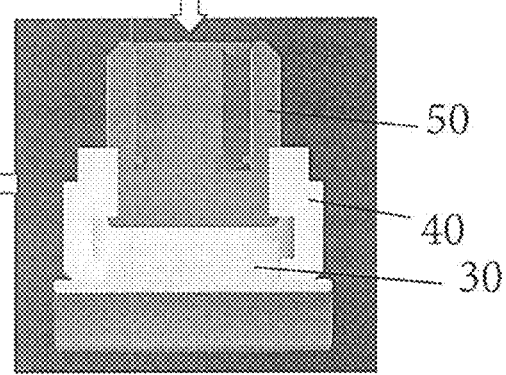
FIG. 6 depicts a cross sectional view of the integrated locking cap assembly of FIG. 5, in which the saddle is not engaged with a locking cap.

As depicted in FIGS. 6 and 7, the saddle features into the bottom of the cap such that the saddle axis is perpendicular to the locking cap wings. FIG. 6 depicts a cross sectional view of the integrated locking cap assembly of FIG. 5, in which the saddle is not yet engaged with a locking cap. FIG. 7 depicts a cross sectional view of the integrated locking cap assembly of FIG. 6, after the saddle has been turned e.g., 90 degrees to engage the saddle with the locking cap. By way of example, a 90 degree turn engages a ledge 32 on the top portion of the saddle with a groove 44 in the locking cap, preventing separation of the components. A CAM mechanism between the saddle and the cap resists unwanted rotation, and thus temporarily fixes the two components together. The saddle/cap assembly can then be inserted into the screw head using a standard locking cap driver.

FIG. 8 depicts a perspective view of the integrated locking cap assembly of FIG. 7, in which the saddle is engaged with the locking cap. FIG. 9 depicts a perspective view of a pedicle screw 64 assembly having a rod inserted therein and the integrated locking cap assembly of FIG. 8 is inserted over the rod.

FIG. 10 depicts a perspective view of the pedicle screw assembly having a rod inserted therein and the integrated locking cap assembly of FIG. 8 inserted over the rod, after the cap has been rotated to lock the cap. In particular, a 90 degree turn engages the locking cap into the screw head, captures the rod 60, and disengages the saddle 30. The saddle is then clamped to the top of the rod by tightening the locking cap set screw 50. As with the saddle in other embodiments herein, the saddle 30 increases the surface area contact with the rod (in the case of these embodiments, the surface area contact between the locking cap set screw and the top of the PEEK rod) when the set screw is tightened, thus eliminating or decreasing plastic deformation of the rod that might otherwise occur.

FIG. 11 depicts a cross sectional front view of the assembly of FIG. 10 in which the integrated locking cap depicted e.g., in FIG. 8 is configured in a pedicle screw assembly over an elongate rod.

Non-limiting example embodiments of the present invention are directed to rod coupler systems that include a coupling body having a bone fastener, such as a pedicle screw disposed therethrough. The coupling body may have a locking cap inserted therein. Also included is a saddle having a first side, which abuts the cap within the coupling body. The saddle also has a second side opposite said first side, which second side has a concave portion that is configured to receive and contact a rod along at least two lines of contact between said saddle and said rod. The concave portion of the saddle may be shaped so as to substantially correspond to a portion of surface area of the elongate rod. A set screw may be further provided in the locking cap.

The bone fastener may be a pedicle screw. Rod coupling systems provided herein may further include one or more of the elongate rod itself and a set screw disposed in the locking cap.

Also provided are integrated locking cap devices that include a locking cap adapted for attachment to a coupling body and a saddle having a first side, which abuts and is removably attached to the locking cap and has a second side opposite said first side, which second side has a concave portion that is configured to receive and contact a rod along at least two lines of contact between said saddle and said rod. The devices may further include a set screw disposed in the locking cap.

Further provided are methods that include inserting a rod into a coupling body such that the rod abuts a bone fastener in the coupling body, and adding a saddle over said rod, within the coupling body, wherein the saddle has a first side abutting a locking cap, a second side opposite said first side, which second side has a concave portion that is configured to abut said rod along at least two lines of contact between said saddle and said rod. The methods may further include securing the cap to the saddle, securing the cap to the coupling body, and/or tightening the cap over the rod. Also, it should be noted that according to example methods the saddle and or cap may be added to the coupling body prior to inserting the rod there-between.

According to further example embodiments, the rod may be added to a system that includes both an integrated locking cap (i.e., a saddle integrated with the locking cap) and a saddle insert that abuts a bone fastener, such that saddles contact multiple sides of the rod.

Example embodiments of integrated locking caps build a saddle or saddle configuration into the cap itself, eliminating extra steps in surgery.

Further example embodiments include polyaxial screws or locking caps having a concave portion configured to abut an elongate rod along at least two lines of contact between the polyaxial screw and/or the locking cap and the rod.

Figure 12:
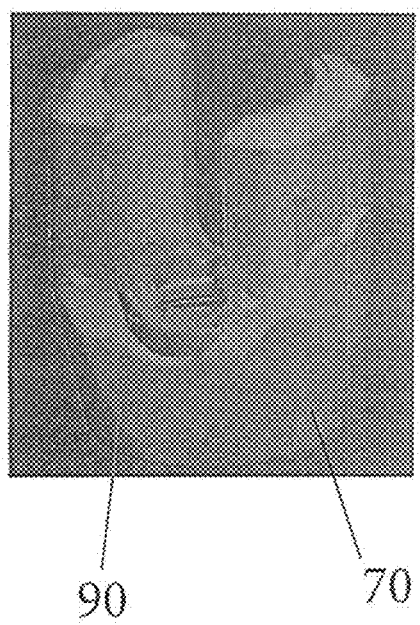
FIG. 12 depicts a perspective view of polyaxial screw in which the head is configured to have a concave portion for receiving a rod in accordance with non-limiting example embodiments.
Figure 13:
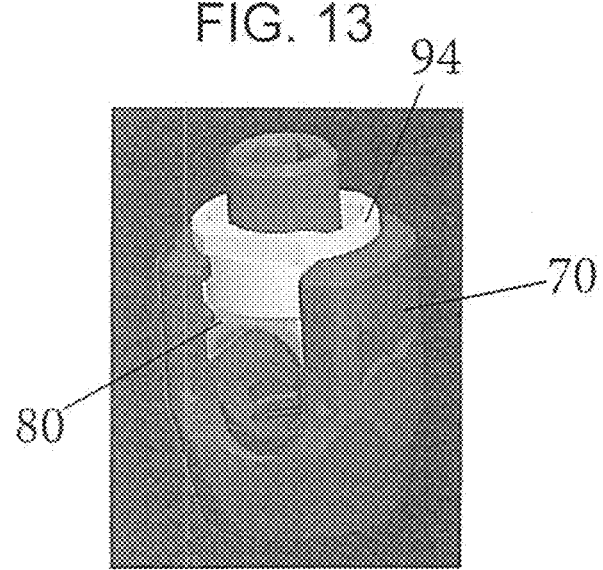
FIG. 13 depicts a perspective view of polyaxial screw depicted in FIG. 12 having a locking cap in accordance with non-limiting example embodiments.

Examples of novel screw head embodiments are depicted in FIGS. 12-13, which allow for surface area contact on both sides of the rod to be increased, eliminating possible plastic deformation of the rod. These embodiments feature e.g., a polyaxial screw tulip head 70 that incorporates a saddle feature 90 into the surface in contact with a rod to be inserted therein (See FIG. 12). The saddle feature may be incorporated into the wedge, clamp, and/or tulip itself. The design may be used in conjunction with an incorporated locking cap 94 that has a saddle type feature 80 (See FIG. 13). This design greatly increases the surface area contact with the rod on top and bottom of the rod and will essentially eliminate plastic deformation of the rod upon final tightening.

Thus, the present invention provides a polyaxial screw having a portion adapted for insertion into bone and a head having a concave portion configured to abut an elongate rod along at least two lines of contact between the polyaxial screw and the rod.

Further non-limiting example embodiments include specially designed inserts, locking caps and/or unique rod shapes, which will increase the surface area contact with rods, particularly those made of PEEK, to reduce notching of the rods. Thus, according to non-limiting example embodiments, titanium screws (rod screws) may be used, even with rods that include PEEK.

By way of example, saddles are provided that include a first side configured to be attached (e.g., detachably attached) to a bone fastener or to a locking cap for a coupling body; and a second side opposite the first side of the saddle, the second side having a concave portion configured to abut an elongate rod along at least two lines of contact between the saddle and the elongate rod.

Figure 14:
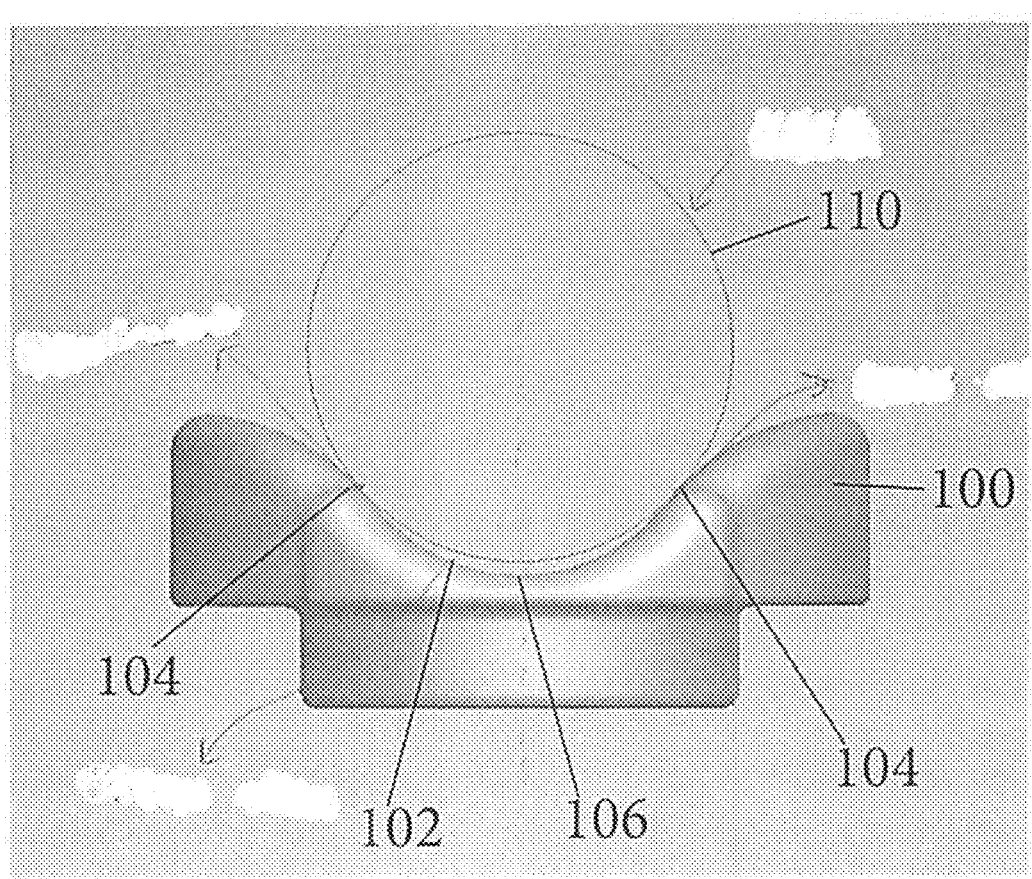
FIG. 14 depicts a front view of a saddle which may be used in accordance with non-limiting example embodiments, which has a smaller radius than the radius of a rod to be inserted therein.

By way of non-limiting example embodiment, FIG. 14 depicts embodiments in which a saddle insert 100 is provided, in which the saddle insert is configured to either abut the bone fastener or abut (or be integrated with) a locking cap, on a first side of the saddle (bottom of the saddle in FIG. 14), and which has a concave portion on a second side of the saddle (top of the saddle in FIG. 14). In these example embodiments, the concave portion of the saddle may have a smaller radius 106 than the radius of an elongate rod 110 to be inserted therein. FIG. 14 demonstrates that the undersized radius 102 creates two tangent lines of contact 104 between the saddle and the rod, rather than a single line of contact. The increased surface area of contact between the saddle and the rod, decreases stress on the rod. Having little or no contact between the rod and the saddle at the center of the saddle 106, eliminates stress risers.

Thus, non-limiting embodiments of the present invention include a saddle having a first side and a second side, the first side being configured to contact a screw or a cap, and the second side being configured with a concave portion having a radius smaller than the radius of a rod to come into contact with at least two tangent lines of said saddle.

Figure 23A:
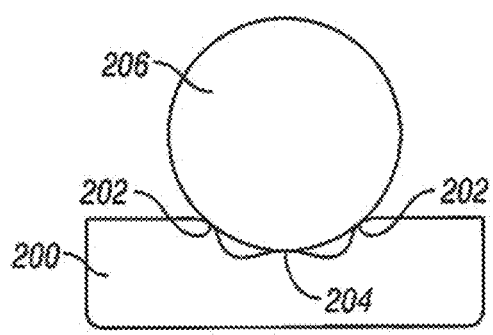
FIGS. 23A and 23B depict front (A) and side (B) cross sectional views of a dimple interface of a saddle with a rod in accordance with non-limiting example embodiments.
Figure 23B:
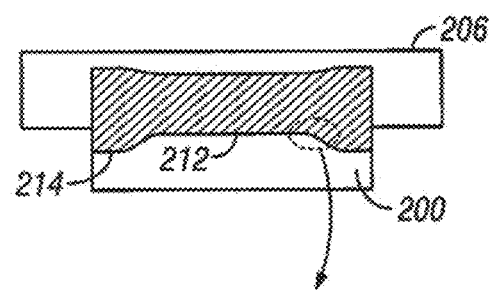

Further example embodiments may include a saddle (again either under and/or over the rod), which has a smaller radius than the radius of an elongate rod to be inserted therein, and which further includes one or more dimples within the radius, such that there are three or more lines of contact between the elongate rod and the saddle, as depicted for example in FIG. 23. In particular, FIG. 23 depicts front (A) and side (B) cross sectional views of a dimple interface of a saddle 200 with a rod 206 in accordance with non-limiting example embodiments. In the depicted embodiments a rod 206 contacts the saddle 200 at at least two lines of contact 202, which extends much of the length of saddle. The dimple 204 also extends much of the length of the saddle as shown as reference numeral 212, in the cross sectional side view of FIG. 23B, having drop offs 214 on either side of the dimple. Contact is also made between the rod and the saddle at at least one dimple 204 in the saddle. The dimple eliminates sharp edge contact and reduces stress risers.

Figure 15:
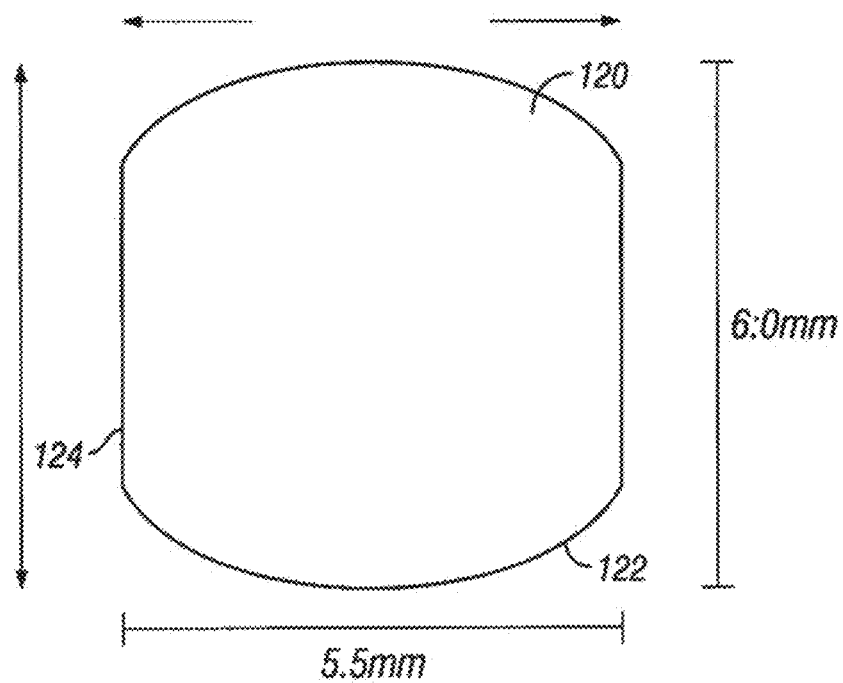
FIG. 15 depicts non-limiting example embodiments of an obrand rod which may be used in accordance with the present invention.

FIG. 15 depicts non-limiting example embodiments of an obrand rod which may be used in accordance with the present invention. In particular, FIG. 15 depicts a rod shape that may have e.g., two interlocking circles connected by flats 124 on either side. This configuration allows an ultimately larger rod to fit in a screw system. 122 is the bottom of a first, lower circle, 120 is the top of an upper circle. Larger A/P dimensions are believed to increase strength, while still fitting in the screw. Thus, combining the height of two circles is believed to be advantageous. Accordingly, provided herein is an elongate rod configured for a rod coupler system, which includes two elongate curved sides and two elongate flat sides.

Figure 16:
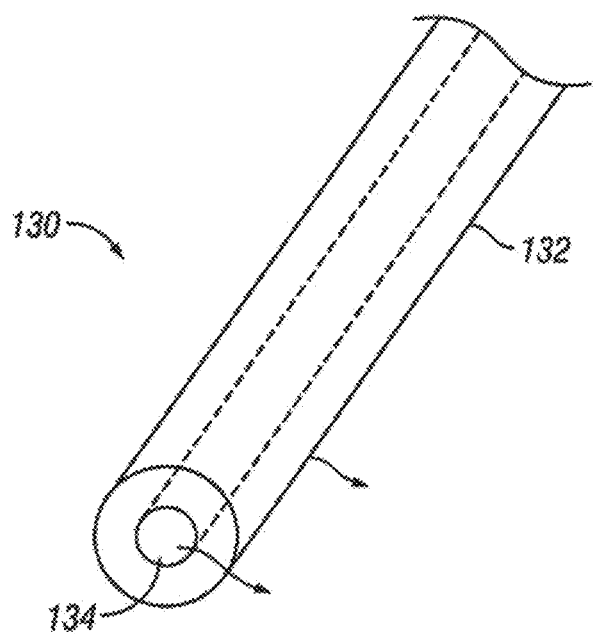
FIG. 16 depicts a non-limiting example embodiment of a composite rod that may be used in accordance with the present invention.

FIG. 16 depicts a non-limiting example embodiment of a composite rod 130 that may be used in accordance with the present invention. In these embodiments, a titanium rod 134 may be pressed into a tube 132 that is made of PEEK. Optionally, additional materials such as stainless steel, alloys, PCU, and other biocompatible materials can also be pressed into the tube 132. According to other example embodiments, the PEEK outer layer may be added to the outside of the titanium rod. The inclusion of titanium in the composite rod adds stiffness and strength to the PEEK material forming part of the rod. Titanium allows the same strength in a smaller rod. Titanium also allows for visibility of the rod on an x-ray.

Figure 17:
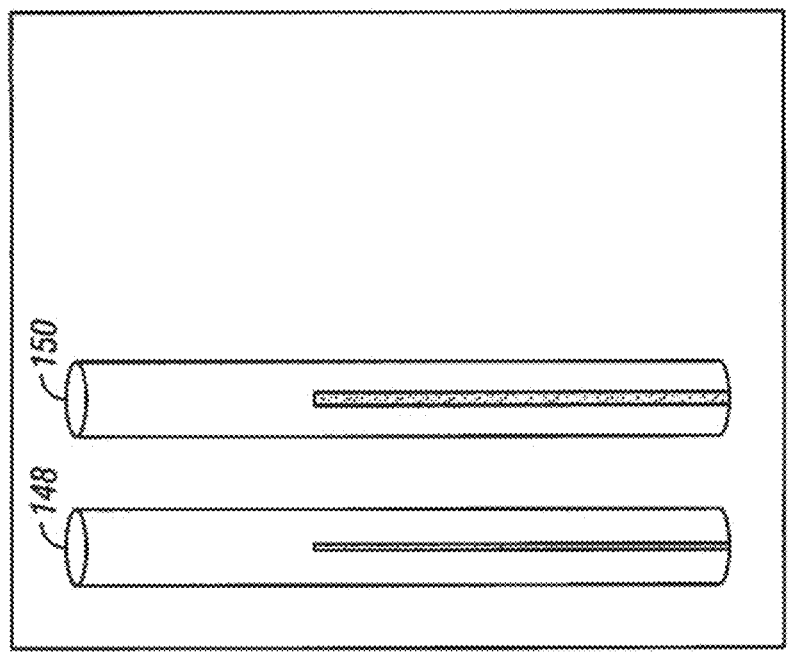
FIG. 17 depicts example PEEK rods that may be used in accordance with the present invention, which offer various levels of stiffness.
Figure 18:
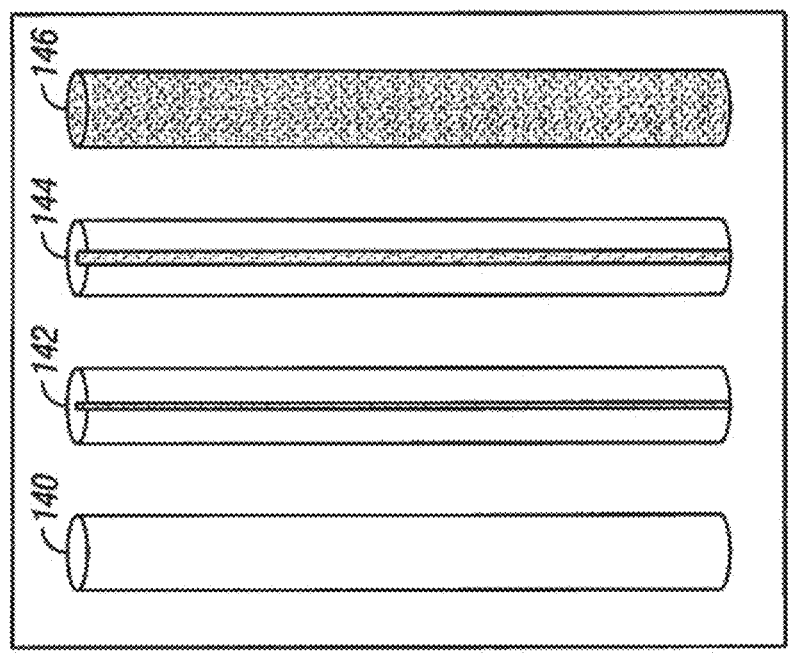
FIG. 18 depicts example PEEK rods that may be used in accordance with the present invention, which also offer various levels of stiffness and depicts topping off.

FIGS. 17 and 18 depict example PEEK rods that may be used in accordance with the present invention, which offer various levels of stiffness. FIG. 17 in particular, depicts various examples of rods having different amounts of titanium forming part of the rod. The rods range from a PEEK rod having no titanium therein 140 (least stiff) to a PEEK rod having a small inside portion of titanium 142, to a PEEK rod having more titanium 144 to a full titanium rod 146 (more stiff). This system offers various levels of stiffness for surgeon preference and possibly topping off at the end of the rod, as depicted in FIG. 18. FIG. 18 shows for example two rods 148 and 150, corresponding roughly to the rods 142 and 144 from FIG. 17, having PEEK portions topping off the rods to add variable stiffness. The stiffness of various rods provided herein, is afforded by titanium rods of various diameters molded within or wrapped around PEEK.

This provided herein are elongate rods configured for a rod coupler system, in which the rod is a composite rod having a first inner portion of titanium and a second outer portion that includes PEEK.

Figure 19:
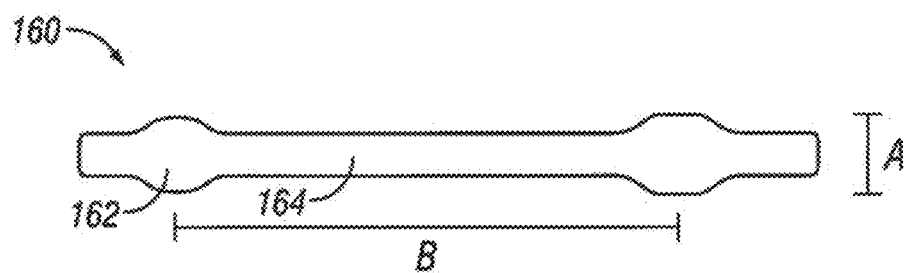
FIG. 19 depicts examples of barreled rods in accordance with non-limiting example embodiments.

FIG. 19 depicts examples of barreled rods 160 in accordance with non-limiting example embodiments. In particular, FIG. 19 depicts example configurations of rods that may be used to increase the diameter A of the rod when it sits in pedicle screws, according to example embodiments provided herein. In particular, barrels 162 are provided near one or both ends of a rod 164. According to non-limiting examples, such barreled rods may be of different lengths B, and may be made of different materials. For example, barreled rods may include titanium or PEEK or some combination thereof (e.g., composite embodiments as described herein). The barreled rods allow for flexibility while strengthening a rod/screw interface.

Figure 20:
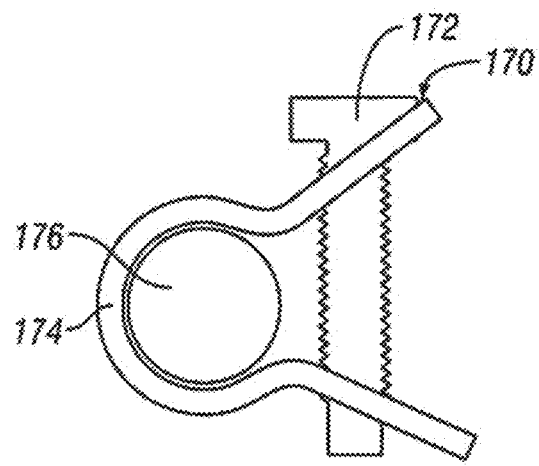
FIG. 20 depicts a posted screw system that may be used in accordance with non-limiting example embodiments.

FIG. 20 depicts a posted screw system that may be used in accordance with non-limiting example embodiments. In particular, FIG. 20 depicts a posted screw system 170 that may be used with a stabilization system. The posted screw system provides a system and method for attaching a rod to a screw using a collet. In particular, the collet 174 may be used to lock a rod 176 to a screw 172. In some embodiments, the collet is provided around a rod and then the screw is inserted through openings in the collet. When the screw is tightened, the collet also tightens around the rod by circumferential pressure. Such systems have a larger surface area contact than other systems. Additionally, such systems provide equal force all around the rod, so there is little or no deformation of the rod. Tightening the screw forces the collet to lock onto the rod.

Thus, example systems may include a screw that passes through at least two portions of a collet, and optionally a rod passing therethrough as well.

Also included are methods of fixing a rod which include passing a rod through a collet and tightening a screw that passes through two or more holes of the collet.

Figure 21:
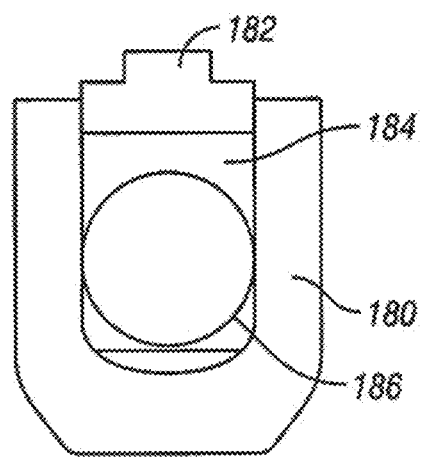
FIG. 21 depicts a collet system that may be used in accordance with the non-limiting example embodiments.
Figure 22:
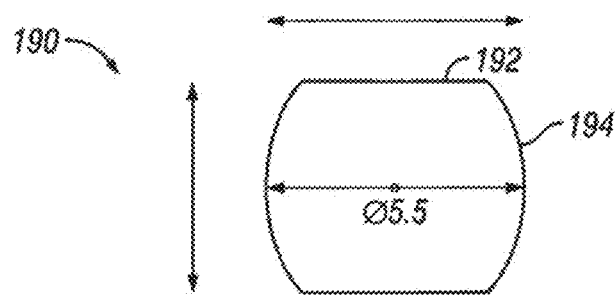
FIG. 22 depicts a cross sectional view of an example rod having flats that may be used in accordance with the present invention.

FIG. 21 depicts a different collet system that may be used in accordance with the non-limiting example embodiments, for example with a spinal stabilization system. In these embodiments a rod is inserted into a collet. Tightening a set screw 182/184 compresses the collet 180 to lock the rod 186. As with other embodiments, devices, systems and methods of these embodiments, may include any number of different kinds of screws and/or rods FIG. 22 depicts a cross sectional view of an example rod having flats that may be used in accordance with the present invention. FIG. 22 depicts for example a rod 190 that has a cross sectional configuration that is relatively flat on each of two sides 192 and may be curved on two sides 194 that extend in an anterior-posterior direction. In such embodiments, a set screw may lock on to the flat side and therefore increase surface area contact.

Also provided are integrated locking caps that include a locking cap adapted for attachment to a coupling body, and a saddle having a first side of said saddle removably attached to the locking cap, and a second side of the saddle opposite the first side, the second side having a concave portion configured to receive and abut an elongate rod along at least two lines of contact between the saddle and the elongate rod.

FIGS. 24-29 depict further examples of integrated locking cap embodiments. In particular, they involve a specially designed insert and locking cap which will increase the surface area contact with the PEEK rods to reduce notching of the rod.

FIGS. 24-29 feature a saddle insert 310 with two grooves 312, 314 oriented at 90 degrees from each other, an initial insertion groove 312 and a rod interface groove 314. Both grooves have a diameter matching that of the rod, such as a PEEK rod. In other embodiments, one groove will have a slightly oversized diameter and one groove will have a slightly undersized diameter. In some embodiments, the rod interface groove 314 can be undersized to advantageously provide at least two lines of contact. The saddle insert features into the bottom of a modified locking cap 320. The insert interfaces with a channel cut into the locking cap to couple the saddle with the cap rotationally while still allowing it to translate axially to capture the rod. Axial movement is to be controlled by the locking cap set screw. Advantageously, the locking cap 320 and saddle insert 310 are connected together such that they will rotate with each other. In some embodiments, the saddle insert includes a tongue feature (shown in FIG. 24) that mates with a groove in the locking cap 320 to secure the two components together.

FIG. 24 depicts an exploded view of an integrated saddle-locking cap design. In FIG. 24, the saddle insert 310 is depicted with multiple grooves 312 and 314. The locking cap 320 is depicted separated from the saddle. Devices and systems may include the saddle insert and locking cap already attached to one another, or separated, such that they may be later attached.

According to example embodiments, the saddle insert 310 snaps onto the bottom of the set screw locking it onto the screw while still allowing it to rotate independently of the screw. The saddle screw assembly is loaded into the modified locking cap such that the saddle tongue slides into the mating groove on the cap. This fixes the caps movement rotationally with the locking cap while still allowing axial movement.

This cap can be inserted and locked using a standard locking cap driver. A ninety degree turn engages the locking cap 320 with the screw head, captures the rod, and aligns the rod interface groove with the rod. The saddle is then clamped into place by tightening the locking cap set screw. The saddle moves axially with regards to the cap but rotates freely with regard to the set screw. In some embodiments, the saddle 310 will move in upward and downward translation relative to the locking cap 320. Advantageously, the saddle increases the surface area contact between the locking cap set screw 340 and the top of the rod. This increased surface area decreases the pressure on the PEEK rod when the set screw 340 is final tightened, eliminating significant plastic deformation.

FIG. 25 depicts a side view of an integrated saddle-locking cap design fully assembled.

Figure 26:
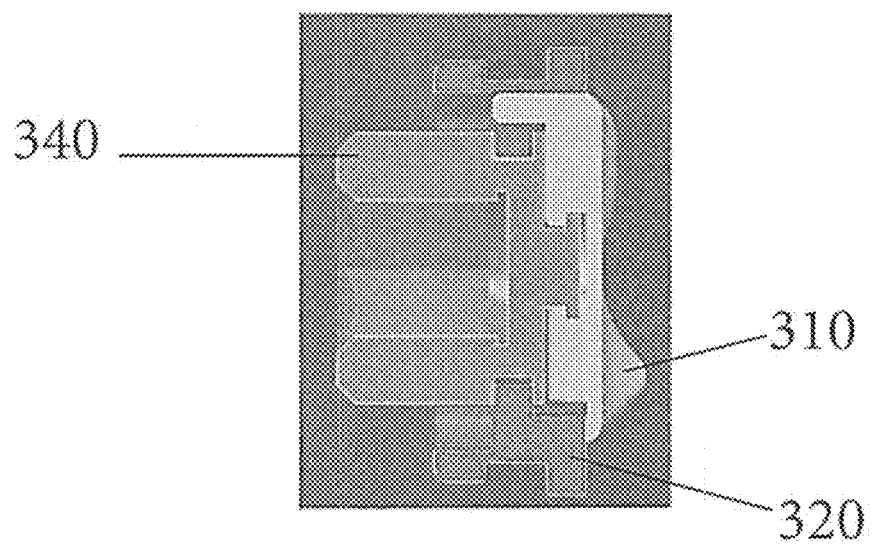
FIG. 26 depicts a side, cross-sectional view of a fully assembled saddle-locking cap design showing a tongue and groove.

FIG. 26 depicts a cross-section view of fully assembled saddle-locking cap design showing tongue and groove attachment. In particular, the figure shows how the saddle attaches to the set screw through the locking cap with a cross-sectional front view of a rod 330 depicted.

Figure 27:
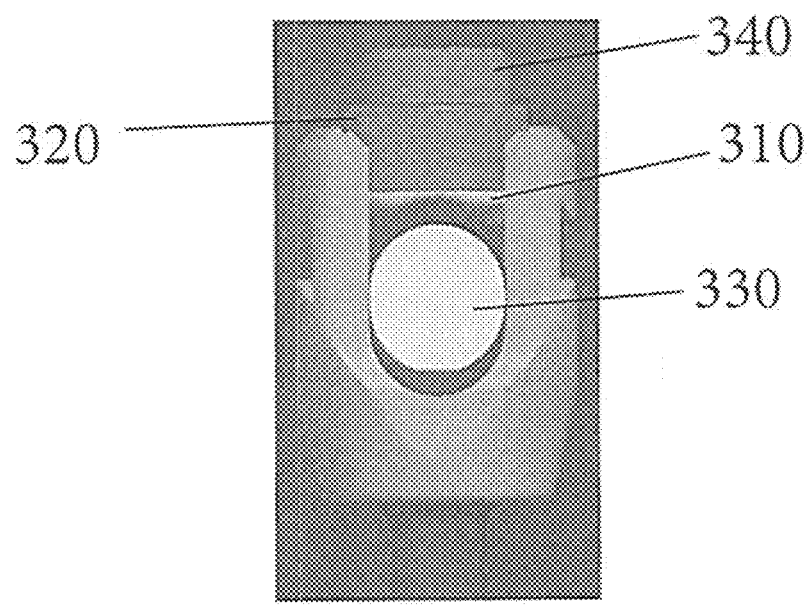
FIG. 27 depicts a front view of a saddle-locking cap design inserted into standard screw head.

FIG. 27 depicts a saddle-locking cap design inserted into standard screw head. FIG. 28 depicts a saddle-locking cap design rotated 90 degrees from its position in FIG. 27 (as can be seen e.g., by the saddle 310 configuration in each figure) and locked into place.

FIG. 29 depicts the integrated locking cap of FIGS. 27 and 28, which has been inserted into a standard screw head, and which has been locked into place as in FIG. 28 and further having had the set screw tightened and the saddle advanced locking the rod.

A method of inserting and using the rod coupler system will now be described with respect to FIGS. 28 and 29. After a rod 330 has been inserted into a coupling body, the integrated locking cap 320 and saddle 310 (e.g., coupled by a tongue-and-groove feature) can be provided. The locking cap 320 includes a bore for receiving a set screw 340 therethrough. Once the integrated locking cap 320 and saddle 310 are deposited in the coupling body, the locking cap 320 and saddle 310 can be rotated (e.g., about 90 degrees) within the coupling body. This advantageously secures the integrated locking cap 320 and saddle 310 to the coupling body and desirably orients the bottom of the saddle 310 such that the saddle opening aligns with the rod member 330.

With respect to FIG. 29, once the integrated locking cap 320 and saddle 310 are properly oriented within the coupling body, the set screw 340 can be downwardly threaded using a screwdriver. As the set screw 340 is downwardly threaded through the bore in the locking cap 320, the distal end of the set screw 340 pushes down on the surface of the saddle 310, which also translates downward onto the rod member 330. The saddle 310 thus compresses the rod member 330, thereby securing the rod member 330 in the coupling body, as shown in FIG. 29.

Advantages of the devices depicted in FIGS. 24-29 include that the devices increase the surface area contact between the locking cap and the screw head, and the PEEK rod, which decreases the amount of plastic deformation in the rod. This allows stabilization systems for example, to become compatible with the use of PEEK rods or other rods described herein, increasing the versatility of both systems. These embodiments are advantageous in the use of instrumentation that is familiar to both the surgeon and the sales force. The use of any of the rods set forth herein is contemplated with regard to these embodiments, including e.g., rods having PEEK, rods of titanium and rods that include combinations of both materials, such as the composite rods discussed herein. Also contemplated are potentially differently shaped rods as discussed herein, so long as the saddle is configured to accommodate the rod shape or vice versa.

The integrated locking cap builds the saddle into the cap itself, eliminating any extra steps in surgery. Fixing the saddle insert onto the set screw allows for easy revision as loosening the set screw and removing the locking cap removes the saddle at the same time without requiring extra instrumentation or additional steps.

Other example embodiments include kits that include one or more components of the present devices and systems. For example, kits may include at least one coupling body having a bone fastener disposed therethrough, and a saddle. The saddle has a first side, which is configured so as to abut the bone fastener within the coupling body and a second side of the saddle opposite the first side, the second side having a concave portion configured to receive and support a rod along at least two lines of contact between the saddle and the rod. These kits may also include on or more of the following components: a locking cap, a set screw, a rod, a tool for assembling a rod coupler system or portions thereof, a tool for inserting a rod coupler system into a patient, a tool for tightening a set screw so as to secure a rod within a rod coupler system assembled using the kit components; and/or instructions for use and/or assembly of a rod coupler system provided herein.

According to example embodiments, at least two components of the kit may be preassembled together within the kit. For example, within a kit a bone fastener and saddle may be provided already assembled within a coupling body, and one or more additional components such as a locking cap and/or elongate rod may optionally be separately provided within the kit. Alternatively, individual components may be provided that may be put together for example by a technician or physician.

All or parts of the present systems may come pre-assembled, for example with the screw and saddle already being pre-inserted into the coupling body, or the parts may be provided separately for example in the form of a kit, and assembled by a technician or surgeon.

Thus, the cap system may include a locking cap configured to fit at least partially within a locking body; and a saddle abutting said locking cap, said saddle having a concave portion that substantially corresponds to a portion of surface area of the rod, and being configured to accept the rod therein. Example systems may further include one or more of the following: cap or a set screw disposed in said cap, and the rod itself. All or parts of the system may come pre-assembled, for example with the screw and saddle already being pre-inserted into the coupling body, or the parts may be individual, for example in the form of a kit, for being put together. Example kits may provide further information or directions regarding assembly. Further provided herein are methods of assembling the rod coupler systems provided herein, and methods of using the present rod couplers that include inserting the couplers into a patient.

Also provided are kits that include a locking cap adapted for a coupling body and a saddle having a first side, adapted to abut and attach to the locking cap and a second side opposite said first side, which second side has a concave portion that is configured to receive and contact a rod along at least two lines of contact between said saddle and said rod. In the kits, the locking cap and the saddle may be pre-attached to one another (e.g., removably attached to one another), or they may be separately provided. The kits may further include a set screw.

Provided kits may also include a coupling body having a bone fastener, such as a pedicle screw. Further examples of kits according to the present invention may include one or more additional components such as a rod, a tool for assembling the present systems or portions thereof, a tool for inserting the present devices or systems into a patient, a tool for tightening a set screw so as to secure a rod within the present systems assembled using the kit components; and instructions for use or assembly of systems comprising the kit components.

According to non-limiting example embodiments, at least two components may be preassembled together within the kit.

The present invention may include methods of assembling the present rod coupler systems. According to non-limiting example embodiments, portions of the assembly may take place outside a patient, while other portions of the assembly may be performed by a surgeon during the process of inserting the assembly into a patient. For example, in non-limiting example embodiments, a saddle as provided herein insert may increase the surface area contact through a step of placing the saddle/insert into the bottom of the screw head before the saddle/screw assembly is inserted into the pedicle of a patient.

Methods may also include methods of treating a patient in need thereof, which include inserting one or more of the present systems or devices into a patient to provide support to a portion of the body of the patient. For example, in some embodiments, the devices and methods described herein are configured to provide support to a spine or back of a patient. In other embodiments, other portions of the body of the patient are supported by the devices.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An integrated locking cap comprising:
    a saddle having a first side configured to abut an elongate rod and a second side opposite the first side;
    a locking cap contacting the second side of the saddle, wherein when the saddle is turned 90 degrees relative to the locking cap, the saddle is attached to the locking cap; and
    a set screw disposed through the locking cap.

2. The integrated locking cap of claim 1, wherein the saddle is attached to the locking cap by a ledge on a top portion of the saddle that fits within a groove of the locking cap.

3. The integrated locking cap of claim 1, wherein the locking cap includes two opposed wings configured to engage a coupling body.

4. The integrated locking cap of claim 1, wherein the first side of the saddle has a concave portion.

5. The integrated locking cap of claim 1, wherein the first side of the saddle has at least two lines of contact between the saddle and the elongate rod.

6. An integrated locking cap comprising:
    a saddle having a first side configured to abut an elongate rod and a second side opposite the first side;
    a locking cap contacting the second side of the saddle, wherein in a first assembled position, the saddle is attached to the locking cap, and in a second assembled position, the saddle is not attached to the locking cap; and
    a set screw disposed through the cap.

7. The integrated locking cap of claim 6, wherein the saddle is attached to the locking cap by a ledge on a top portion of the saddle that fits within in a groove of the locking cap.

8. The integrated locking cap of claim 6, wherein the locking cap includes two opposed wings configured to engage a coupling body.

9. The integrated locking cap of claim 6, wherein the first side of the saddle has a concave portion.

10. The integrated locking cap of claim 6, wherein the first side of the saddle has at least two lines of contact between the saddle and the elongate rod.

11. A rod coupler system comprising:
    a coupling body;
    an elongate rod configured to be received in the coupling body;
    an integrated locking cap configured to be received in the coupling body and secure the elongate rod therein, the integrated locking cap comprises:
        a saddle having a first side configured to abut the elongate rod and a second side opposite the first side;
        a cap contacting the second side of the saddle, wherein when the saddle is turned 90 degrees relative to the cap, the saddle is attached to the cap; and
        a set screw disposed through the cap.

12. The rod coupler system of claim 11, wherein the set screw applies a downward pressure on the elongate rod to lock the elongate rod in position.

13. The rod coupler system of claim 11, wherein the locking cap includes a threaded opening and the set screw is threadedly received in the threaded opening.

14. The rod coupler system of claim 11, wherein the coupling body has a bone fastener disposed therethrough.

15. The rod coupler system of claim 14, wherein the bone fastener comprises a pedicle screw.

16. The rod coupler system of claim 11, wherein the elongate rod is formed of PEEK.

17. The rod coupler system of claim 11, wherein the saddle is attached to the locking cap by a ledge on a top portion of the saddle that fits within in a groove of the locking cap.

18. The rod coupler system of claim 11, wherein the locking cap includes two opposed wings configured to engage a coupling body.

19. The rod coupler system of claim 11, wherein the first side of the saddle has a concave portion.

20. The rod coupler system of claim 11, wherein the first side of the saddle has at least two lines of contact between the saddle and the elongate rod.

\* \* \* \* \*